US010286040B2

(12) United States Patent
Lee et al.

(10) Patent No.: US 10,286,040 B2
(45) Date of Patent: May 14, 2019

(54) COMPOSITION CONTAINING PALMULTANG EXTRACT FOR PROMOTING PROLIFERATION OF STEM CELLS DERIVED FROM BONE MARROW

(71) Applicant: COMPREHENSIVE AND INTEGRATIVE MEDICINE INSTITUTE, Daegu (KR)

(72) Inventors: Chang Hyeong Lee, Daegu (KR); Sang Gyung Kim, Daegu (KR); Im Hee Shin, Daegu (KR); Seung Mo Kim, Daegu (KR); Joon Seok Byun, Daegu (KR); Ki Cheul Sohn, Daegu (KR); Sae Kwang Ku, Daegu (KR)

(73) Assignee: COMPREHENSIVE AND INTEGRATIVE MEDICINE INSTITUTE, Daegu (KR)

( * ) Notice: Subject to any disclaimer, the term of this patent is extended or adjusted under 35 U.S.C. 154(b) by 0 days.

(21) Appl. No.: 15/854,613

(22) Filed: Dec. 26, 2017

(65) Prior Publication Data

US 2018/0185447 A1 Jul. 5, 2018

Related U.S. Application Data

(63) Continuation of application No. 14/888,636, filed as application No. PCT/KR2014/003909 on May 1, 2014, now abandoned.

(30) Foreign Application Priority Data

May 3, 2013 (KR) .......................... 10-2013-0050323

(51) Int. Cl.
| | | |
|---|---|---|
| *A61K 38/00* | (2006.01) | |
| *A61K 38/19* | (2006.01) | |
| *C12N 5/0789* | (2010.01) | |
| *A61K 36/804* | (2006.01) | |
| *A61K 36/076* | (2006.01) | |
| *A61K 36/232* | (2006.01) | |
| *A61K 36/234* | (2006.01) | |
| *A61K 36/258* | (2006.01) | |
| *A61K 36/284* | (2006.01) | |
| *A61K 36/484* | (2006.01) | |
| *A61K 36/65* | (2006.01) | |
| *A61K 36/07* | (2006.01) | |
| *A61K 36/64* | (2006.01) | |

(52) U.S. Cl.
CPC ............ *A61K 38/193* (2013.01); *A61K 36/07* (2013.01); *A61K 36/076* (2013.01); *A61K 36/232* (2013.01); *A61K 36/234* (2013.01); *A61K 36/258* (2013.01); *A61K 36/284* (2013.01); *A61K 36/484* (2013.01); *A61K 36/64* (2013.01); *A61K 36/65* (2013.01); *A61K 36/804* (2013.01); *C12N 5/0647* (2013.01); *C12N 2500/76* (2013.01)

(58) Field of Classification Search
None
See application file for complete search history.

(56) References Cited

U.S. PATENT DOCUMENTS 8,394,430 B2 * 3/2013 Lee ........................ A61K 33/04
424/725

FOREIGN PATENT DOCUMENTS

| KR | 100440863 B1 | 7/2004 |
| KR | 1020050042046 A | 5/2005 |
| KR | 20080042761 A | 5/2008 |
| KR | 1020100029507 A | 3/2010 |
| KR | 102012001474 A | 2/2012 |

OTHER PUBLICATIONS

Yun et a. 2007. Biol. Pharm. Bull 30:337-342.*
Kim et al. 2018. Evidence-Based Complementary and Alterntive Med. 2018:Article ID 3479083.*
http://pharmalink.kr/skfda.php?page=1801&act=search&searchopt=&startday=&endday=&sortorder=&rows_list=20, 2000.*
International Search Report for International Application No. PCT/KR2014/003909 (dated Aug. 27, 2014) (2 Pages).
Makinoda et al.,"Granulocyte Colony-Stimulating Factor (G-CSF) in the Mechanism of Human Ovulation and its Clinical Usefulness", Current Medicinal Chemistry, 2008, vol. 15, pp. 604-613.
Joo et al., "The Effect of Palmultang on Ovarian Functions and Differential Gene Expression of Caspase-3, MAPK and MPG in Female Mice", The Journal of Oriental Obstetrics & Gynecology,2007, vol. 20, No. 3, pp. 91-110.
Oh et al., "Inhibitory Effects of Palmultang on Inflammatory Mediator Production Related to Suppression of NF-kB and MAPK Pathways and Induction of H0-1 Expression in Macrophages", Int. J. Mol. Sci., 2014, vol. 15, pp. 8443-8457.
Metcalf, "The Granulocyte-Macrophage Colony-Stimulating Factors", Science, vol. 229, pp. 16-22.

* cited by examiner

*Primary Examiner* — Shulamith H Shafer
(74) *Attorney, Agent, or Firm* — Lucas & Mercanti, LLP

(57) ABSTRACT

The present invention relates to a composition for promoting the proliferation of stem cells derived from bone marrow using a palmultang extract, and more specifically, to a composition for promoting the proliferation of stem cells derived from bone marrow by administering a granulocyte colony-stimulating factor to a subject and then administering the palmultang extract to the subject. The composition of the present invention remarkably reduces side effects, such as enlargement of the spleen, which are caused by the administration of G-CSF alone for proliferation and differentiation of the stem cells, through administration in combination with the palmultang extract, thereby further promoting the proliferation and differentiation of stem cells.

3 Claims, 18 Drawing Sheets

COMPOSITION CONTAINING PALMULTANG EXTRACT FOR PROMOTING PROLIFERATION OF STEM CELLS DERIVED FROM BONE MARROW

CROSS-REFERENCE TO RELATED APPLICATION

This application is a Continuation of U.S. application Ser. No. 14/888,636, filed Nov. 2, 2015, which is a 371 of International Application No. PCT/KR2014/003909, filed May 1, 2014, which claims the benefit of Korean Patent Application No. 10-2013-0050323, filed May 3, 2013, the contents of each of which are incorporated herein by reference.

TECHNICAL FIELD

The present invention relates to a composition for promoting proliferation of stem cells derived from bone marrow including a palmultang extract.

BACKGROUND ART

"Stem cells" generally refers to undifferentiated cells that can differentiate into various cells constituting biological tissues and can be obtained from individual tissues of embryos, fetuses, and adults in a cell stage prior to cell differentiation. Among various stem cells, blood adult stem cells are stem cells that are derived from bone marrow and may have totipotency to differentiate into all type of cells constituting organs and blood of human bodies.

Among these, bone-marrow-derived stem cells are considered as an ultimate tool for treating diseases such as hematologic cancers, lymphoma, and bone marrow failure. In recent years, bone-marrow-derived stem cells have been transplanted for various purposes. In particular, when it is difficult to transplant organs into patients suffering from terminal kidney and liver diseases, attempts have been made to promote regeneration of the liver and kidneys by autologous transplantation of bone-marrow-derived stem cells.

To promote cell differentiation and division after the autologous transplantation of bone-marrow-derived stem cells, a human recombinant granulocyte colony-stimulating factor (hG-CSF) is administered in a full dose. However, the proliferation of stem cells and the mobilization into blood do not occur in approximately 5 to 30% of patients, and various side effects such as cardiac infarction, cerebral infarction, pyrexia, ostalgia, splenomegaly, and ruptures are known to be caused by administration of hG-CSF (Masoud et al., 2008; Fox et al., 2009). In particular, the use of hG-CSF is limited. Therefore, a new alternative to enhance an effect of hG-CSF on proliferation of bone-marrow-derived stem cells and reduce such side effects is needed.

Meanwhile, palmultang is a representative qi-strengthening medicine widely used in the field of Oriental medicine. Literally, palmultang refers to a recipe including eight medicinal herbs. Sagunjatang is known as a qi-strengthening medicine and a samultang is known as a blood-nourishing medicine, and palmultang is a recipe obtained by combination of these two medicines. Sagunjatang includes the four medicinal herbs *Panax ginseng*, *Atractylodes ovata*, *Glyceyrrhiza uralensis*, and *Wolfiporia extensa*, and samultang includes the four medicinal herbs *Rehmannia glutinosa*, *Paeonia lactiflora*, *Cnidium officinale*, and *Angelica gigas*. Sagunjatang is known to promote metabolic actions, enhance immune functions, and improve blood-increasing activities and digestive absorption functions, and samultang is known to be applied to weakness from a disease.

DISCLOSURE

Technical Problem

Therefore, the present invention is designed to solve the problems of the prior art, and therefore it is an object of the present invention to provide a composition for promoting proliferation of bone-marrow-derived stem cells using a palmultang extract.

However, the technical objects of the present invention are not limited thereto, and other objects of the present invention which are not disclosed herein will become more apparent to those of ordinary skill in the art by describing in detail exemplary embodiments thereof.

Technical Solution

To solve the above problems, according to an aspect of the present invention, there is provided a composition for promoting proliferation of bone-marrow-derived stem cells, which includes a granulocyte colony-stimulating factor and a palmultang extract.

According to one exemplary embodiment of the present invention, the stimulating factor and the palmultang extract may be formulated by being mixed in advance, or may be formulated separately.

According to another exemplary embodiment of the present invention, the stimulating factor and the palmultang extract may be administered parenterally, orally, locoregionally, or percutaneously.

According to still another exemplary embodiment of the present invention, administration of the palmultang extract may begin within 30 minutes after administration of the stimulating factor.

Advantageous Effects

The composition for promoting proliferation of stem cells, which includes the palmultang extract provided in the present invention as an active ingredient, includes a human recombinant granulocyte colony-stimulating factor (hG-CSF) and the palmultang extract, and thus can be useful in promoting proliferation and differentiation of stem cells when the composition is administered prior to transplantation of stem cells.

Also, the composition according to one exemplary embodiment of the present invention can be used as a new alternative to solve the technical problems of the prior art, for example, side effects such as cardiac infarction, cerebral infarction, pyrexia, ostalgia, splenomegaly, and rupture, when proliferation of stem cells is induced by administering hG-CSF to promote proliferation and differentiation of the stem cells.

BEST MODE

Figure 1:
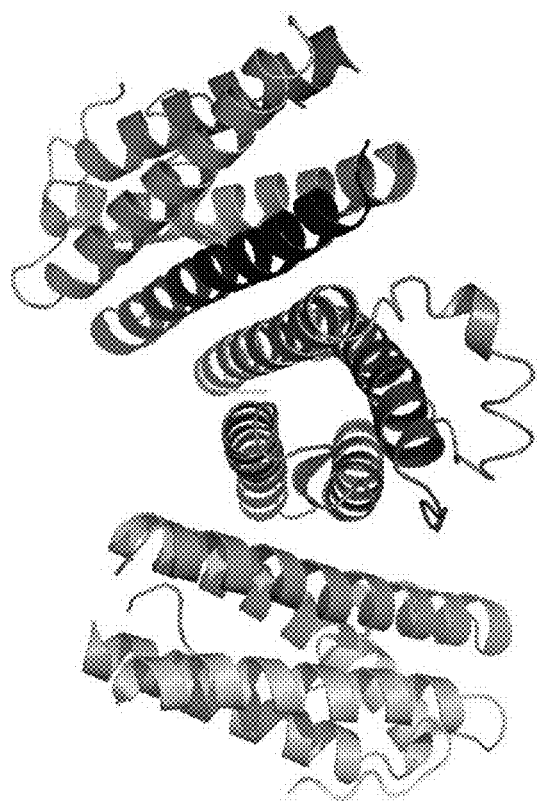
FIG. 1 is a diagram showing a structure of hG-CSF used in the present invention.

The present inventors have focused on one medicinal herb in order to develop a composition capable of reducing various side effects caused when a human recombinant granulocyte colony-stimulating factor is administered to promote cell differentiation and division after transplantation of bone-marrow-derived stem cells and increasing production of the bone-marrow-derived stem cells, and found that the medicinal herb has an excellent effect of promoting proliferation and differentiation of stein cells when the medicinal herb is added to palmultang. Therefore, the present invention has been completed based on these facts.

Therefore, according to an aspect of the present invention, there is provided a composition for promoting proliferation of bone-marrow-derived stein cells, which included a granulocyte colony-stimulating factor and a palmultang extract.

The term "palmultang extract" used in the present invention refers to an extract obtained by extracting eight medicinal herbs. The eight medicinal herbs are *Panax ginseng, Atractylodes ovata, Glycyrrhiza uralensis, Wolfiporia extensa, Rehmannia glutinosa, Paeonia lactiflora, Cnidium officinale*, and *Angelica gigas*.

According to one exemplary embodiment of the present invention, the stimulating factor and the palmultang extract may be formulated by being mixed in advance, or may be formulated separately.

The palmultang extract may be administered within 30 minutes, preferably 15 minutes, and most preferably 5 minutes after administration of the granulocyte colony-stimulating factor, but the present invention is not limited thereto.

The granulocyte colony-stimulating factor used in the present invention is characterized in that it s a human recombinant granulocyte colony-stimulating factor, but the present invention is not limited thereto.

The granulocyte colony-stimulating factor and the palmultang extract may be administered parenterally, orally, locoregionally, or percutaneously. Preferably, the palmultang extract may be administered orally, but a route of administration may be properly chosen by those skilled in the related art according to a condition and body weight of a patient, the severity of a disease, administration duration, etc.

In the present invention, the term 'subject' refers to a target requiring treatment of a disease, and, more particularly, to a mammal such as a human or a non-human primate, a mouse, a rat, a dog, a cat, a horse, and cattle.

According to another aspect of the present invention, there is provided a pharmaceutical composition for enhancing production of bone-marrow-derived stem cells, which includes a palmultang extract.

The pharmaceutical composition according to one exemplary embodiment of the present invention may include a pharmaceutically acceptable carrier. The pharmaceutically acceptable carrier may include a physiological saline solution, polyethylene glycol, ethanol, vegetable oil, and isopropyl myristate, but the present invention is not limited thereto.

According to one exemplary embodiment of the present invention, a preferred dosage of the pharmaceutical composition may vary according to a condition and body weight of a patient, the severity of a disease, the form of a drug, and a route and time of administration, but may be properly chosen by those skilled in the related art. However, the pharmaceutical composition may be preferably administered at a dose of 0.001 to 300 mg/kg of body weight, and more preferably 0.01 to 200 mg/kg of body weight a day.

The pharmaceutical composition according to one exemplary embodiment of the present invention may be administered to a mammal such as a rat, a mouse, livestock, and a human through various routes of administration. Methods of administration are not particularly limited. For example, the composition may be administered orally, rectally, or by intravenous, intramuscular, subcutaneous, cervical epidural, or intra-cerebroventricular injection.

In the present invention, when the palmultang extract was administered orally after administration of hG-CSF, it was revealed that splenomegaly was relieved when the palmultang extract was orally co-administered within 5 minutes (see Example 2), an increase in weight of the spleen and splenomegaly findings by proliferation of nuclear cells in red pulp was inhibited significantly (p<0.01), no effect on overall proliferation of granulocytes was observed (see Example 3), and proliferation and mobilization of the bone-marrow-derived stem cells by hG-CSF were significantly enhanced (p<0.01) (see Example 4).

Therefore, the composition for promoting proliferation of bone-marrow-derived stem cells, which includes the palmultang extract according to one exemplary embodiment of the present invention has effects of enhancing production of the bone-marrow-derived stem cells and simultaneously reducing various side effects caused when the hG-CSF is administered alone as known in the related art.

Mode for Invention

Hereinafter, preferred embodiments are provided to aid in understanding the present invention. However, it should be understood that detailed description provided herein is merely intended to provide a better understanding of the present invention, but is not intended to limit the scope of the present invention.

EXAMPLES

In these Examples, effects of palmultang, samchulgeon-bitang (also referred to as SCGBT), *Astragalus membranaceus* Bunge var. *membranaceus, Capreolus capreolus ochracea* Thomas, and *Angelica gigas* on medicinal effects and side effects of hG-CSF, particularly on mobilization and splenomegaly of stem cells, were evaluated using Balb/c mice which are often used to mobilize stem cells by means of hG-CSF.

Example 1. Preparation for Experiment 1-1. Preparation of Materials hG-CSF was purchased from Life Technologies (Carlsbad, Calif., USA) to be used, and the structure of the hG-CSF is shown in FIG. 1.

Palmultang (also referred to as 'PMT') was purchased from HanZung Pharmaceutical Co. Ltd. (Daejeon, Korea) to be used, and the components and their amounts in the palmultang are listed in the following Table 1.

TABLE 1

| Herbs | Scientific Names/Produce Region | Amounts (g) |
|---|---|---|
| Angelicae Gigantis Radix | *Angelica gigas* N. | 2.46 |
| Atractylodis Rhizoma | *Atractylodes ovata* (Thunb.) DC. | 2.46 |
| Cnidii Rhizoma | *Cnidium officinale* Makino | 2.26 |
| Ginseng Radix Alba | *Panax ginseng* C. A. Meyer. | 1.6 |
| Glycyrrhizae Radix | *Glycyrrhiza uralensis* Fisch | 1.8 |
| Hoelen | *Poria cocos* Wolf | 0.13 |
| Paeoniae Radix | *Paeonia lactiflora* Pall. | 1.8 |
| Rehmanniae Radix Preparata | *Rehmannia glutinosa* Liboschitz ex Steudel | 3.33 |
| Total | 8 types | 15.84 |

For comparison, SCGBT, *Astragalus membranaceus* Bunge var. *membranaceus, Capreolus capreolus ochracea* Thomas, and *Angelica gigas* were chosen as medicinal materials to compare their effects with the effects of the palmultang. The components and amounts of the medicinal herbs in the SCGBT are listed in the following Table 2.

TABLE 2

| Herbs | Scientific Names/Produce Region | Amounts (g) |
|---|---|---|
| Amomi Fructus | *Amomum xanthiodes* Wallich | 0.16 |
| Atractylodis Rhizoma Alba | *Atractylodes ovata* (Thunb.) DC. | 0.98 |
| Citri Unshii Pericarpium | *Citrus unshiu* S. Marcov. | 0.85 |
| Ginseng Radix Alba | *Panax ginseng* C. A. Meyer. | 0.64 |
| Glycyrrhizae Radix et Rhizoma | *Glycyrrhiza uralensis* Fisch | 0.36 |
| Hawthorn Fruit (Crataegi Fructus) | *Crataegus pinnatifida* Bunge var. *typica* Schneider | 0.93 |
| Hordei Fructus Germiniatus | *Hordeum vulgare* Linn. | 0.34 |
| Zizyphi Fructus | *Zizyphus jujuba* var. *inermis* (Bunge) Rehder | 4.17 |
| Magnoliae Cortex | *Magnolia officinalis* Rehder et Wilson | 0.21 |
| Massa Medicata Fermentata | *Triticum aestivum* L. | 0.67 |
| Paeoniae Radix | *Paeonia lactiflora* Pall. | 0.54 |
| Ponciri Fructus | *Poncinus trifoliata* | 0.58 |
| Hoelen | *Poria cocus* Wolf | 0.05 |
| Zingiberis Rhizona Crudus | *Zingiber officinale* Roscoe | 0.26 |
| Total | 14 types | 10.74 |

1-2. Preparation of Laboratory Animals

In this Example, Balb/c CrSlc mice (6-week-old females, SLC, Shizuoka, Japan) were selected and used as laboratory animals. Seven healthy SPF Balb/c mice were purchased, and acclimatized for 34 days. Thereafter, only the laboratory animals having uniform body weights were chosen and divided into seven groups of ten mice, and used for this experiment as listed in the following Table 3. All the laboratory animals were fasted overnight for 18 hours, a period of which spanned from date on which hG-CSF and medicines were administered up to a final date of autopsy (drinking water was freely supplied), and the subjects were identified using picric acid.

TABLE 3

| Group | Inducer | Test substances and dose (mg/kg/day) | Animal No. |
|---|---|---|---|
| | | GCSF-2012-PD: Effects on hG-CSF-treated mice | |
| Control | Saline 10 ml/kg | Distilled water oral 10 ml/kg [Intact vehicle] | M01~M10 |
| Control | hG-CSF 250 µg/kg | Distilled water oral 10 ml/kg [hG-CSF] | M11~M20 |
| Active | hG-CSF 250 µg/kg | PMT oral (200 mg/kg) [PMT] | M21~M30 |
| Active | hG-CSF 250 µg/kg | SCGBT oral (200 mg/kg) [SCGBT] | M31~M40 |
| Active | hG-CSF 250 µg/kg | AR oral (200 mg/kg) [AR] | M41~M50 |
| Active | hG-CSF 250 µg/kg | CCP oral (200 mg/kg) [CCP] | M51~M60 |
| Active | hG-CSF 250 µg/kg | AGR oral (200 mg/kg) [AGR] | M61~M70 |

1-3. Methods of Administration

Administration of hG-CSF and Candidate Drugs

250 µg/kg of hG-CSF (Life Technologies, Carlsbad, Calif., USA) was continuously subcutaneously administered once a day for 6 days according to the previous methods (Verma et al., 1997; Levesque et al., 2003) to promote proliferation of leukocytes and mobilization of bone-marrow-derived stem cells. Thereafter, 200 mg/kg of each of palmultang, SCGBT, *Astragalus membranaceus* Bunge var. *membranaceus, Capreolus capreolus ochracea* Thomas and *Angelica gigas* extracts was orally administered within 5 minutes after administration of hG-CSF. In this case, the administration was performed once a day for 6 days. All the five natural-substance-derived extracts were dissolved in sterile distilled water, and then forcibly orally administered to the mice at a dose of 10 ml/kg of body weight using a 1 mL syringe with metallic zoned needle, and hG-CSF was dissolved in a physiological saline solution, and then subcutaneously administered into subcutaneous regions of the backs of the mice at a dose of 10 ml/kg. In the hG-CSF control, only an equivalent dose of sterile distilled water was administered instead of the natural-substance-derived extracts, and, in the normal medium control, only equivalent doses of the physiogical saline solution and sterile distilled water were subcutaneously and orally administered instead of the hG-CSF and the natural-substance-derived extract at intervals of 5 minutes. The dose used in this experiment, that is, 200 mg of the natural-substance-derived extract, was chosen based on the results obtained from each animal experiment.

1-4. Observation Items

Changes in body weights and spleen weights, and the number of CD34+ and CD45+ cells as representative markers for labeling bone-marrow-derived stem cells as well as the total number of bone marrow nuclear cells and blood leukocytes in the bone marrow and blood were determined using a fluorescence-activated cell sorting (FACS) method. Also, the number of CD34+ and CD45+ cells per unit area in tissue samples from the spleen and bone marrow was determined using an immunohistochemical method, and the total thickness of the spleen, the amount and diameters of white pulp, and the number of nuclear cells in the spleen red pulp and bone marrow per unit area were also evaluated using an automated image analyzer (iSolution FL ver 9.1, IMT i-solution Inc., Quebec, Canada). To observe clearer changes, the changes (%) in the normal medium control and the hG-CSF control, and the respective changes (%) in the groups to which the natural-substance-derived extract was administered and the hG-CSF control were calculated and compared.

Example 2. Determination of Changes in Body Weight and Weight Gain

Figure 2:
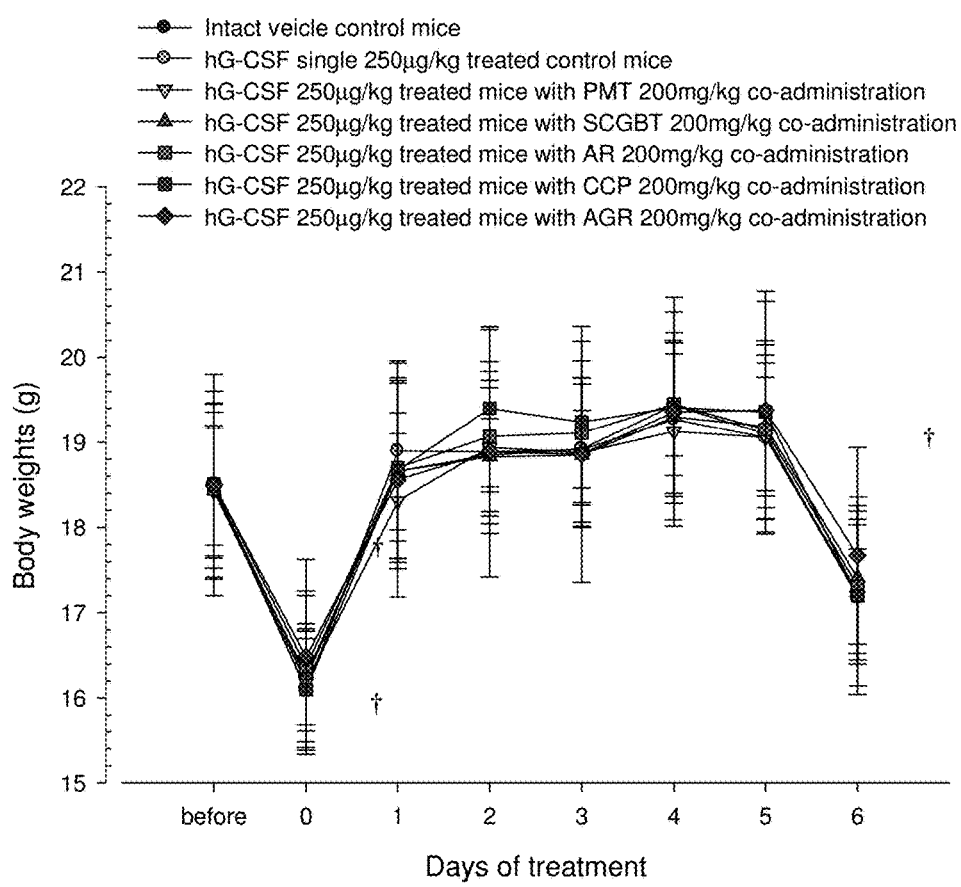
FIG. 2 is a diagram showing changes in body weights and weight gains of mice when hG-CSF or a natural-substance-derived candidate compound is administered.

Based on the observation results, changes in body weight and weight gain were measured, and are listed in Table 4 and shown in FIG. 2. As shown in FIG. 2, it could be seen that the changes in body weight and weight gain associated with administration of the hG-CSF or the natural-substance-derived candidate compound compared to the normal medium control were not shown to be significant for the entire experimental period.

TABLE 4

| Groups | Body weight(g) | | Body weight gains (g) during treatment [B − A] |
|---|---|---|---|
| | At first treatment [A] | Sacrifice [B] | |
| Controls | | | |
| Intact vehicle | 16.24 ± 0.63 | 17.19 ± 0.56 | 0.95 ± 0.44 |
| hG-CSF | 16.10 ± 0.68 | 17.24 ± 0.79 | 1.14 ± 0.36 |

TABLE 4-continued

| Groups | Body weight(g) | | Body weight gains (g) during treatment [B − A] |
|---|---|---|---|
| | At first treatment [A] | Sacrifice [B] | |
| Natural extract orally co-administered | | | |
| PMT | 16.19 ± 0.51 | 17.20 ± 1.06 | 1.01 ± 0.76 |
| SCGBT | 16.27 ± 0.93 | 17.41 ± 0.78 | 1.14 ± 0.55 |
| AR | 16.37 ± 0.89 | 17.31 ± 0.79 | 0.94 ± 0.51 |
| CCP | 16.10 ± 0.71 | 17.20 ± 1.16 | 1.10 ± 0.51 |
| AGR | 16.48 ± 1.15 | 17.67 ± 1.27 | 1.19 ± 0.57 |

Values are expressed mean ± S.D. of 10 mice

However, it was revealed that the weight gain for the entire experimental period of 6 days changed by 20.00% in the hG-CSF control, compared to the normal medium control, and that the weight gains changed by −11.40, 0.00, 17.54, −3.51, and 4.39% in the groups to which the palmultang, SCGBT, *Astragalus membranaceus* Bunge var. *membranaceus, Capreolus capreolus ochracea* Thomas, and *Angelica gigas* extracts (200 mg/kg) were administered, respectively, compared to the hG-CSF control.

Example 3. Determination of Change in Weight of Spleen

Changes in weights of spleens observed in this Example are listed in the following Table 5. In the hG-CSF control, increases in weight of the spleen and relative weight with respect to the body weight caused by splenomegaly were significant ($p<0.01$), compared to the normal medium control. In the groups to which the palmultang and *Angelica gigas* extracts were administered, a decrease in weight of the spleen was shown to be significant ($p<0.01$), compared to the hG-CSF control.

TABLE 5

| Groups | Spleen weights | |
|---|---|---|
| | Absolute (g) | Relative (% of body weight) |
| Controls | | |
| Intact vehicle | 0.066 ± 0.005 | 0.384 ± 0.018 |
| hG-CSF | 0.132 ± 0.012$^a$ | 0.768 ± 0.090$^a$ |
| Natural extract orally co-administered | | |
| PMT | 0.104 ± 0.008$^{ab}$ | 0.608 ± 0.064$^{ab}$ |
| SCGBT | 0.139 ± 0.019$^a$ | 0.803 ± 0.128$^a$ |
| AR | 0.125 ± 0.011$^a$ | 0.721 ± 0.050$^a$ |
| CCP | 0.150 ± 0.018$^{ac}$ | 0.871 ± 0.085$^{ac}$ |
| AGR | 0.109 ± 0.008$^{ab}$ | 0.618 ± 0.061$^{ab}$ |

Figure 3:
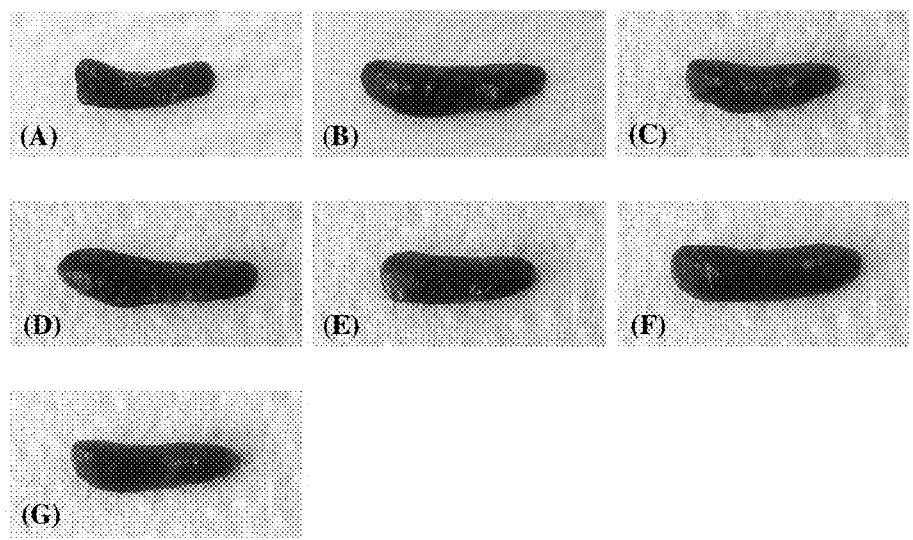
FIG. 3 is a diagram showing the results obtained by determining the sizes of spleens from the mice into which the hG-CSF or the natural-substance-derived candidate compound is administered (A: untreated, B: hG-CSF, C: palmultang+hG-CSF, D: samchulgeonbitang (SCGBT)+hG-CSF, E: *Astragalus membranaceus* Bunge var. *membranaceus*+hG-CSF, F: *Capreolus capreolus ochracea* Thomas+hG-CSF, and G: *Angelica gigas*+hG-CSF).
Figure 4A:
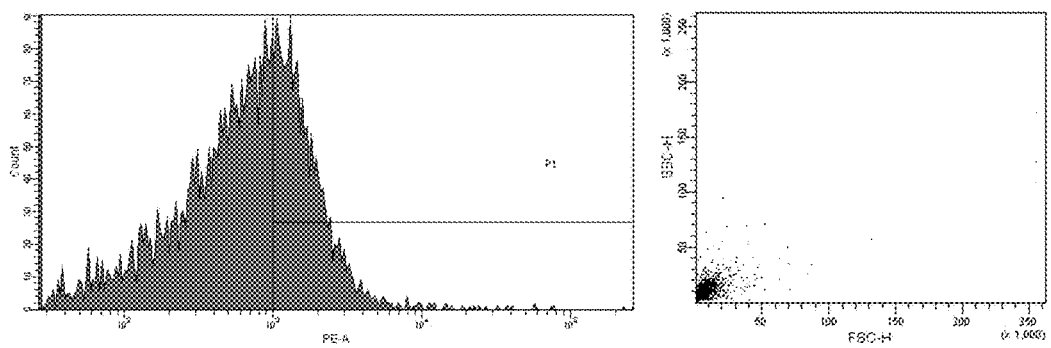
FIGS. 4 and 5 are diagrams showing the results obtained by observing CD34+ cells of the mice into which the hG-CSF or the natural-substance-derived candidate compound is administered using a fluorescence-activated cell sorter (FACS) (A: untreated, B: hG-CSF, C: palmultang+hG-CSF, D: SCGBT+hG-CSF, E: *Astragalus membranaceus* Bunge var. *membranaceus*+hG-CSF, F: *Capreolus capreolus ochracea* Thomas+hG-CSF, and G: *Angelica gigas*+hG-CSF).
Figure 4B:
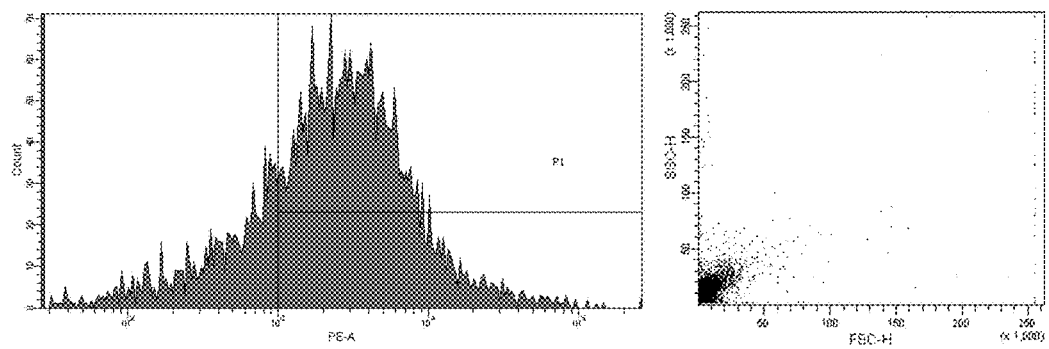
Figure 4C:
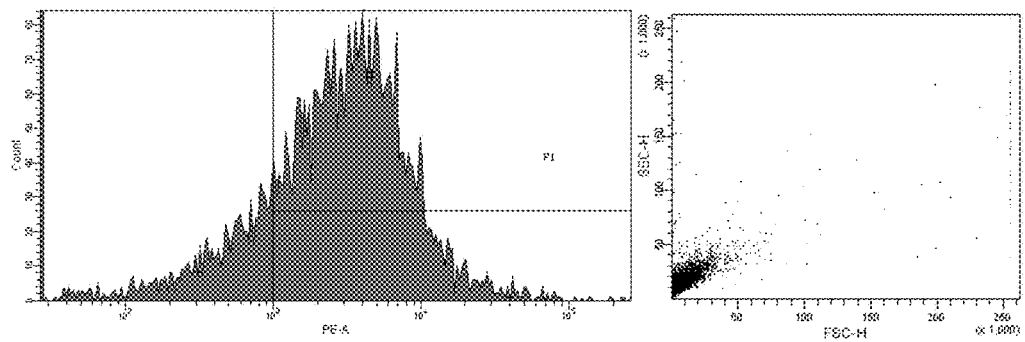
Figure 4D:
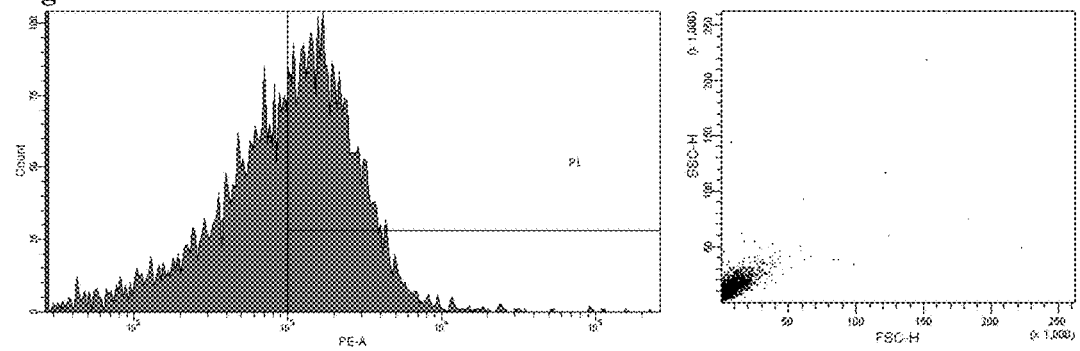
Figure 4E:
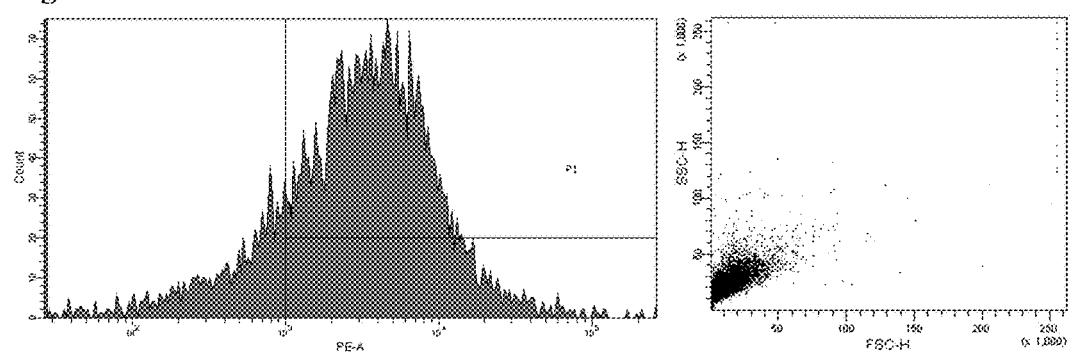
Figure 4F:
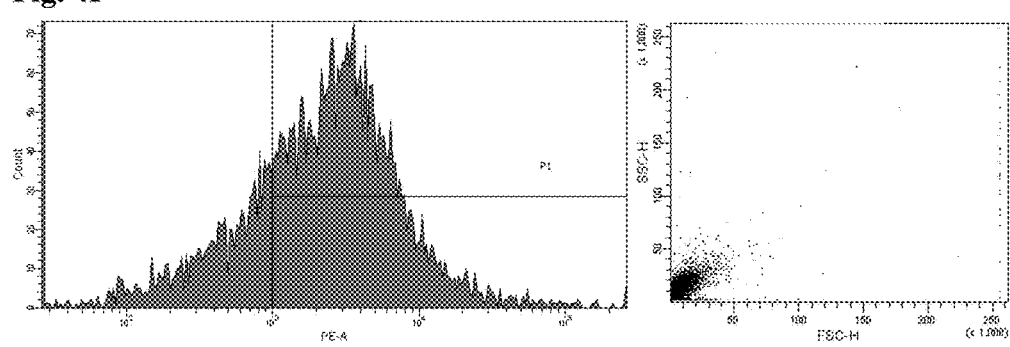
Figure 4G:
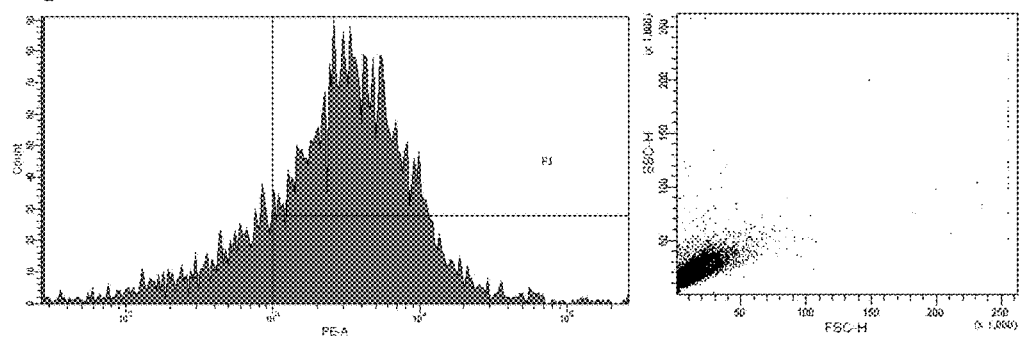
Figure 5A:
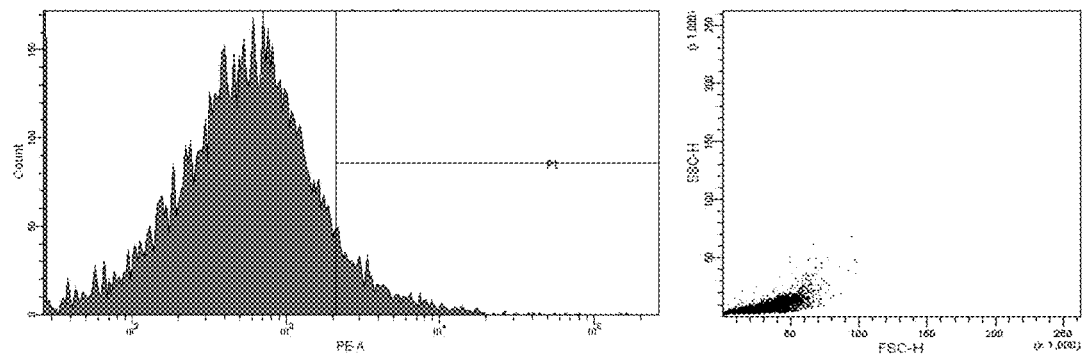
Figure 5B:
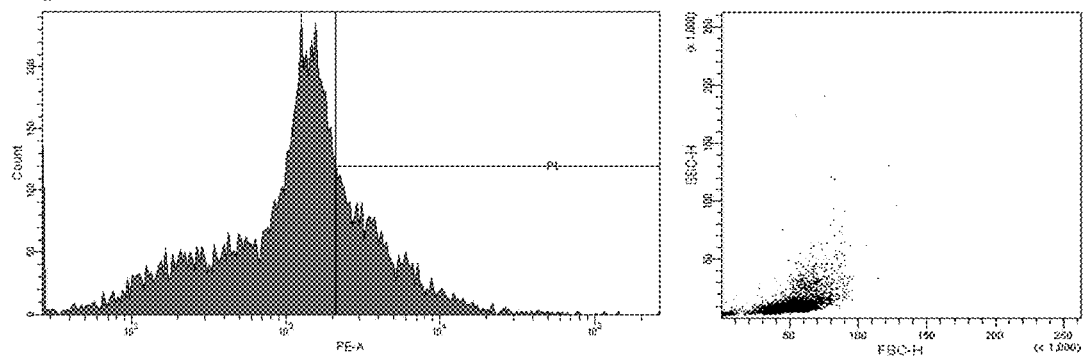
Figure 5C:
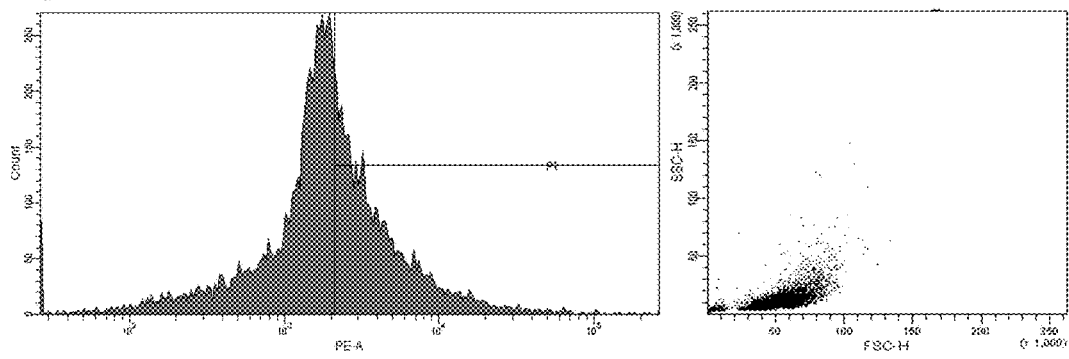
Figure 5D:
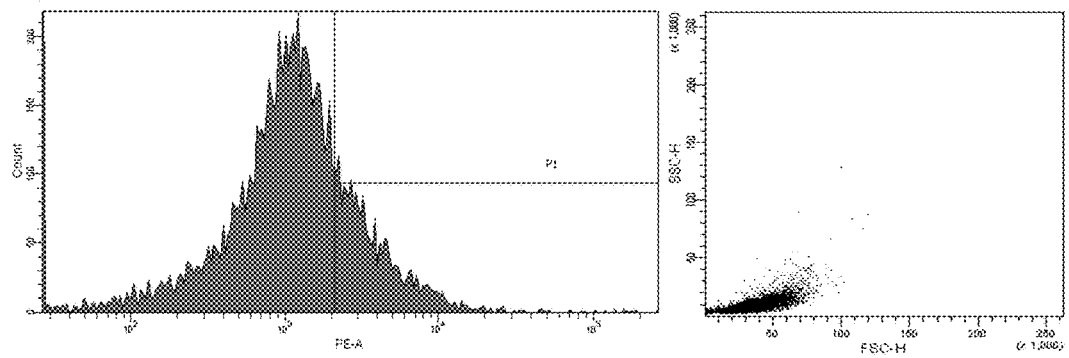
Figure 5E:
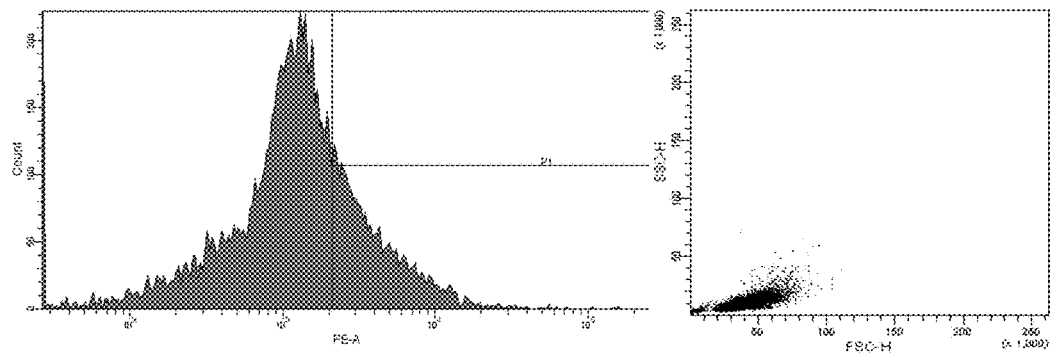
Figure 5F:
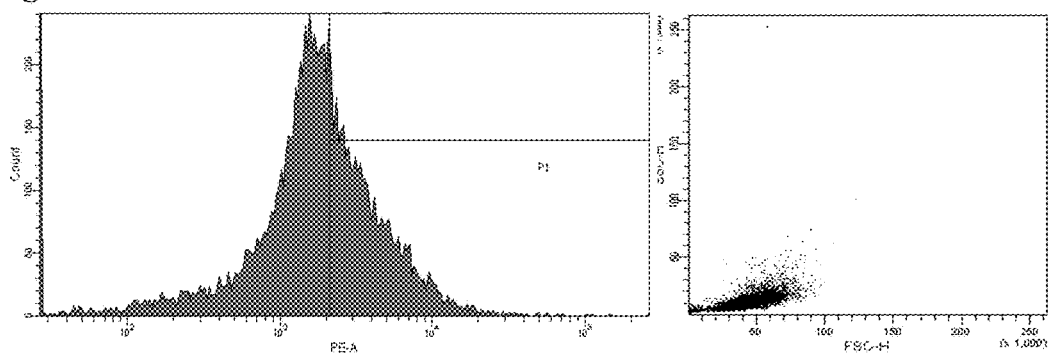
Figure 5G:
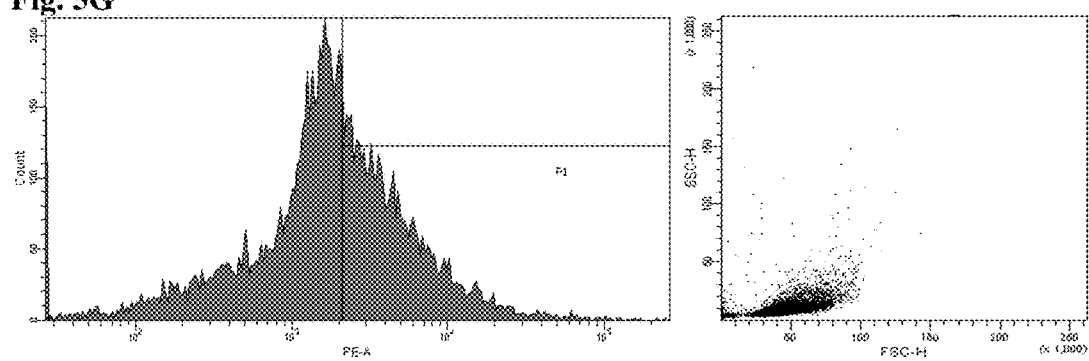
Figure 6A:
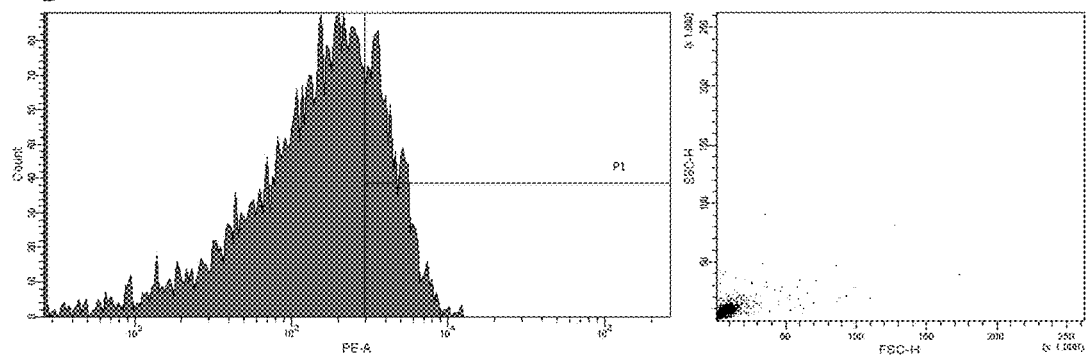
FIGS. 6 and 7 are diagrams showing the results obtained by observing CD45+ cells of the mice into which the hG-CSF or the natural-substance-derived candidate compound is administered using a FACS (A: untreated, B: hG-CSF, C: palmultang+hG-CSF, D: SCGBT+hG-CSF, E: *Astragalus membranaceus* Bunge var. *membranaceus*+hG-CSF, F: *Capreolus capreolus ochracea* Thomas+hG-CSF, and G: *Angelica gigas*+hG-CSF).
Figure 6B:
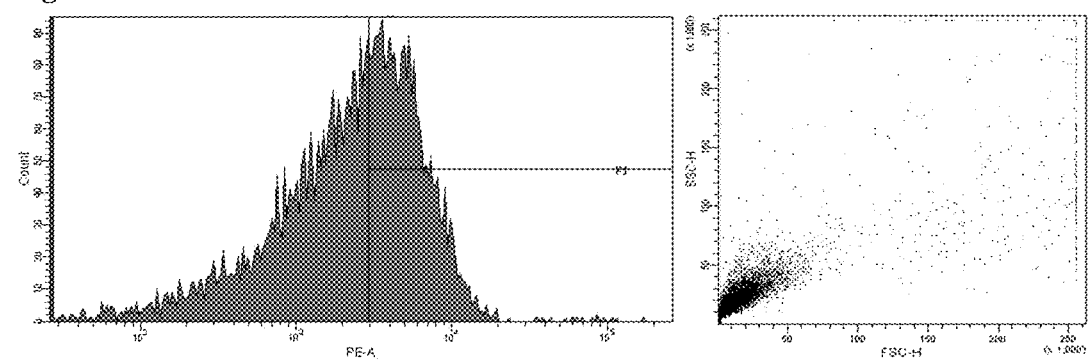
Figure 6C:
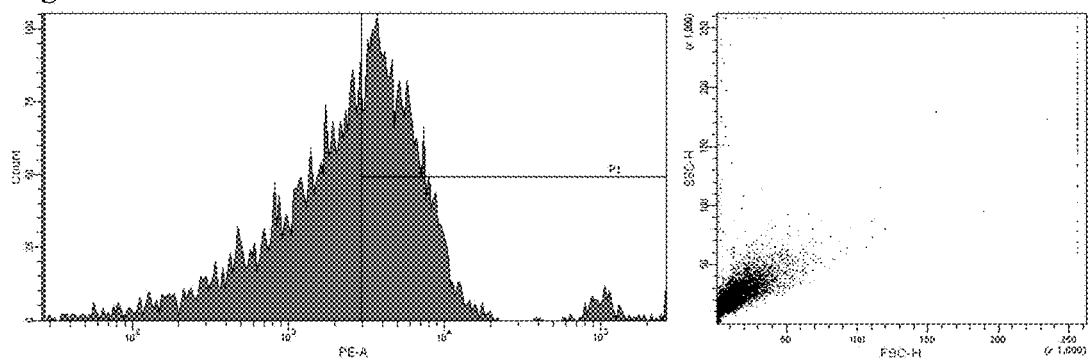
Figure 6D:
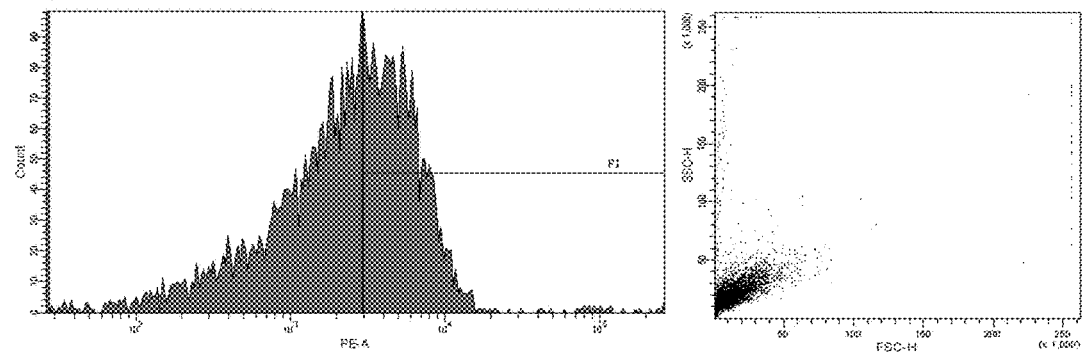
Figure 6E:
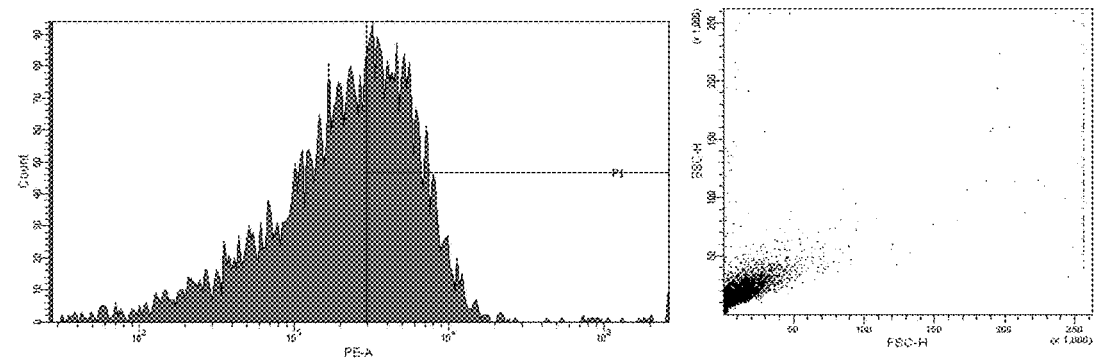
Figure 6F:
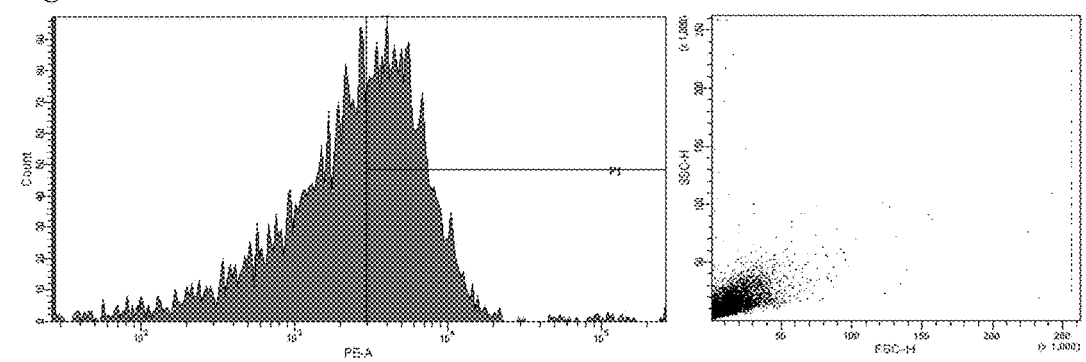
Figure 6G:
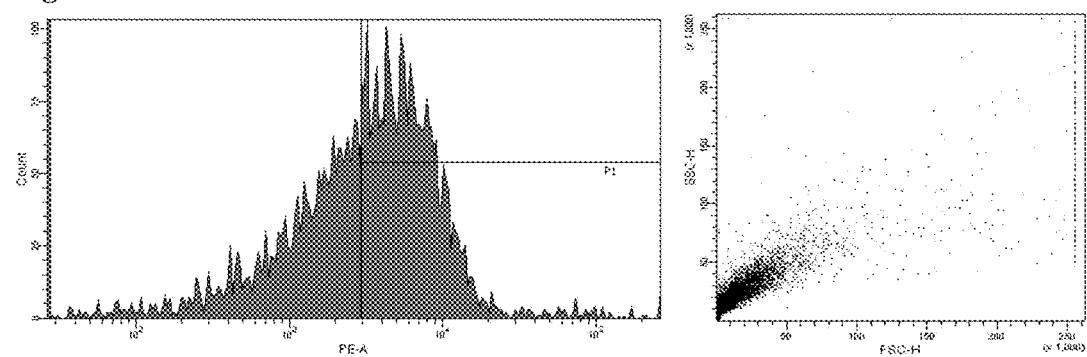
Figure 7A:
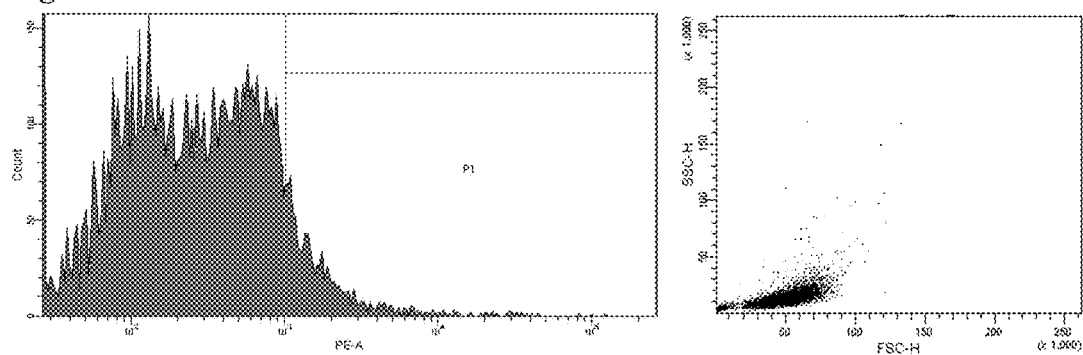
Figure 7B:
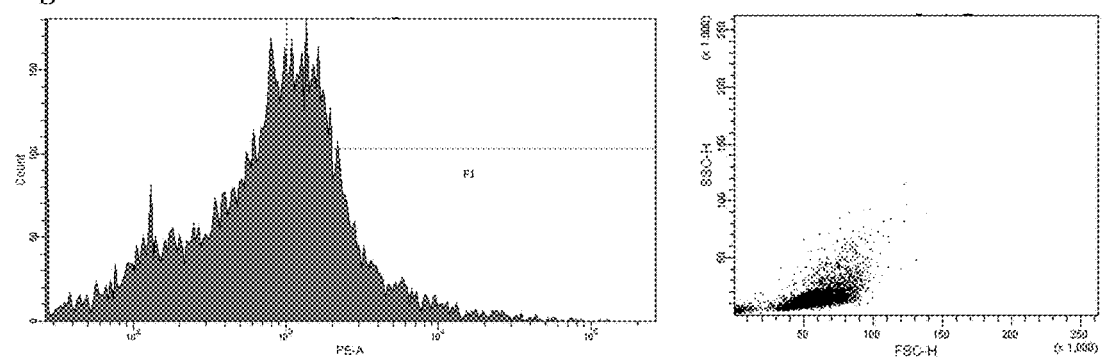
Figure 7C:
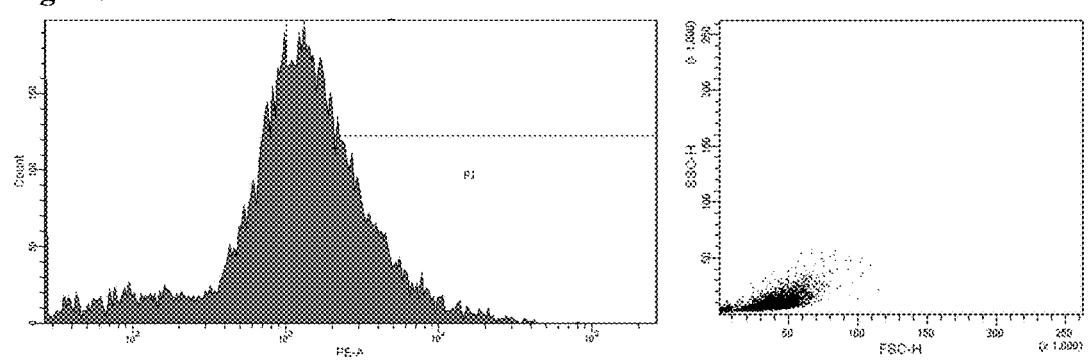
Figure 7D:
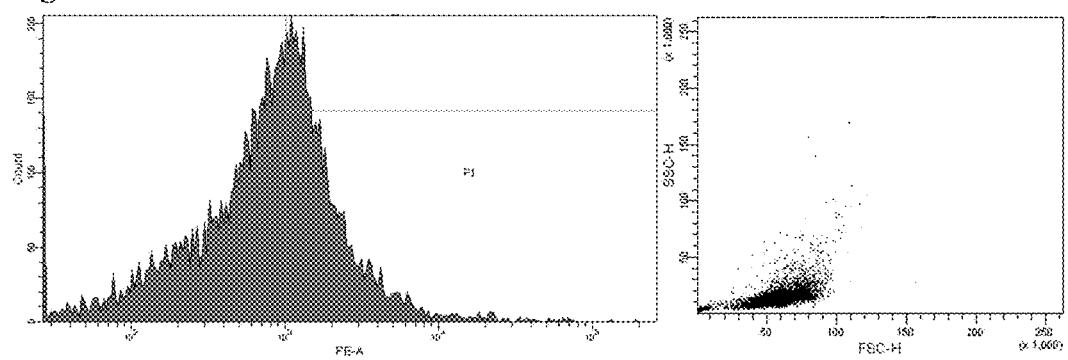
Figure 7E:
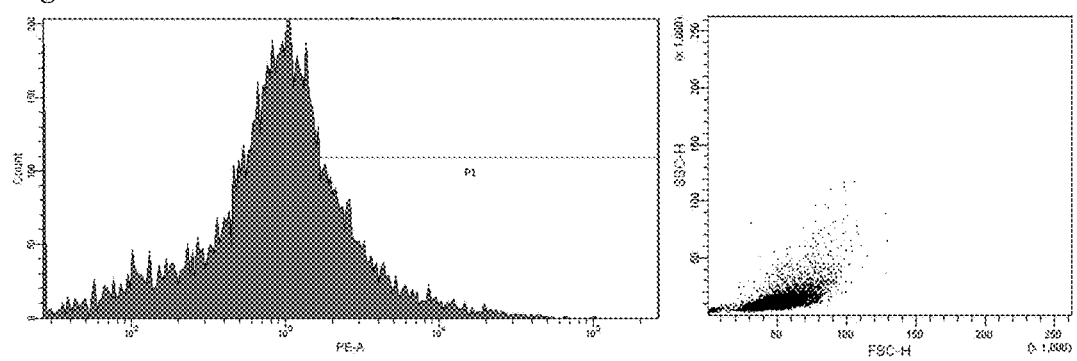
Figure 7F:
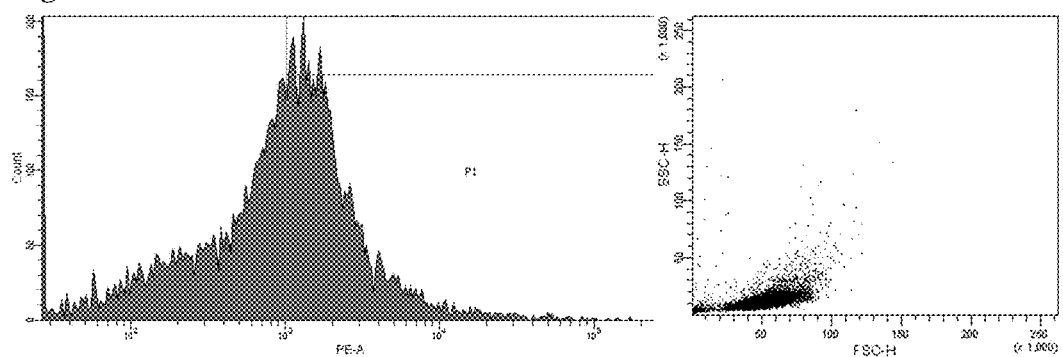
Figure 7G:
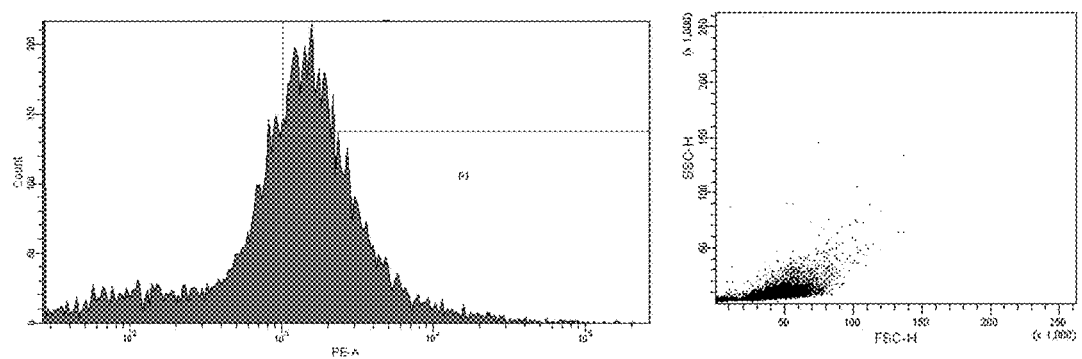

As shown in FIG. 3, it was also revealed that the size of the spleen decreased in the groups to which the palmultang and *Angelica gigas* extracts were administered when observed with naked eye, compared to the normal medium control.

Meanwhile, in the group to which the *Capreolus capreolus ochracea* Thomas extract was administered, increases in absolute and relative weights of the spleen were shown to be significant ($p<0.05$), compared to the hG-CSF control. In the groups to which the SCGBT and *Astragalus membranaceus* Bunge var. *membranaceus* extracts were administered, changes in absolute and relative weights of the spleen were not shown to be significant, compared to the hG-CSF control.

In the hG-CSF control, the absolute weight of the spleen changed by 99.55%, compared to the normal medium control, in the groups to which the palmultang, SCGBT, *Astragalus membranaceus* Bunge var. *membranaceus*, *Capreolus capreolus ochracea* Thomas, and *Angelica gigas* extracts (200 mg/kg) were administered, the absolute weights of the spleens changed by −21.08, 5.61, −5.38, 13.65, and −17.51%, respectively, compared to the hG-CSF control.

In the hG-CSF control, the relative weight of the spleen changed by 99.81%, compared to the normal medium control. In the groups to which the palmultang, SCGBT, *Astragalus membranaceus* Bunge var. *membranaceus*, *Capreolus capreolus ochracea* Thomas, and *Angelica gigas* extracts (200 mg/kg) were administered, the relative weights of the spleens changed by −20.85, 4.57, −6.13, 13.46, and −19.46%, compared to the hG-CSF control.

Based on the experimental results, it was revealed that the side effects (e.g., splenomegaly) of hG-CSF were relieved when the hG-CSF and the palmultang extract were co-administered.

Example 4. Determination of Number of Blood Leukocytes and Bone Marrow Nuclear Cells In this Example, changes in numbers of blood leukocytes and bone marrow nuclear cells were observed. The results are listed in the following Table 6.

TABLE 6

| Groups | Total Cell Counts | |
|---|---|---|
| | Blood leukocytes ($\times 10^3$ cells/µl) | Bone marrow nuclear cells ($\times 10^3$ cells/µl) |
| Controls | | |
| Intact vehicle | 5.06 ± 2.00 | 47.10 ± 20.93 |
| hG-CSF | 53.40 ± 22.63$^a$ | 457.90 ± 129.50$^c$ |
| Natural extract orally co-administered | | |
| PMT | 55.50 ± 17.92$^a$ | 440.80 ± 115.78$^c$ |
| SCGBT | 47.70 ± 13.34$^a$ | 444.10 ± 105.38$^c$ |
| AR | 52.50 ± 11.74$^a$ | 431.90 ± 127.46$^c$ |
| CCP | 73.00 ± 12.94$^{ab}$ | 590.10 ± 134.67$^c$ |
| AGR | 57.10 ± 16.93$^a$ | 444.80 ± 92.76$^c$ |

In the hG-CSF control, increases in total numbers of blood leukocytes and bone marrow nuclear cells were shown to be significant (p<0.01), compared to the normal medium control. However, the increases in the total numbers of blood leukocytes and bone marrow nuclear cells were shown to be significant in the hG-CSF/*Capreolus capreolus ochracea* Thomas co-administered group, but changes in the total number of blood leukocytes and the bone marrow nuclear cells were not shown to be significant in any of the natural substance extract co-administered groups.

In the hG-CSF control, the total number of blood leukocytes changed by 955.34%, compared to the normal medium control. In the groups to which the palmultang, SCGBT, *Astragalus membranaceus* Bunge var. *membranaceus*, *Capreolus capreolus ochracea* Thomas, and *Angelica gigas* extracts (200 mg/kg) were administered, the total numbers of blood leukocytes changed by 3.93, −10.67, −1.69, 36.70, and 6.93%, respectively, compared to the hG-CSF control.

In the hG-CSF control, the total number of bone marrow nuclear cells changed by 872.19%, compared to the normal medium control. In the groups to which the palmultang, SCGBT, *Astragalus membranaceus* Bunge var. *membranaceus*, *Capreolus capreolus ochracea* Thomas, and *Angelica gigas* extracts (200 mg/kg) were administered, the total numbers of bone marrow nuclear cells changed by −3.73, −3.01, −5.68, 28.87, and −2.86%, respectively, compared to the hG-CSF control.

Therefore, it was revealed that the total numbers of blood leukocytes and bone marrow nuclear cells did not increase but remained at similar levels when the palmultang extract was administered, compared to the hG-CSF control.

Example 5. FACS Results: Determination of Changes in Number of CD34+ and CD45+ Cells in Blood and Bone Marrow Changes in the numbers of CD34+ and CD45+ cells in the blood and bone marrow were observed using a FACS method. The results are listed in the following Table 7.

TABLE 7

| | Blood leukocytes | | Bone marrow nuclear cells | |
|---|---|---|---|---|
| Groups | CD34+ cells ($\times 10^2$ cells/µl) | CD45+ cells ($\times 10^2$ cells/µl) | CD34+ cells ($\times 10^2$ cells/µl) | CD45+ cells ($\times 10^2$ cells/µl) |
| Controls | | | | |
| Intact vehicle | 7.93 ± 1.05 | 10.41 ± 1.47 | 16.60 ± 3.76 | 13.16 ± 2.32 |
| hG-CSF | 26.81 ± 6.02$^a$ | 42.94 ± 8.62$^a$ | 30.41 ± 6.69$^a$ | 24.63 ± 3.82$^a$ |
| Natural extract orally co-administered | | | | |
| PMT | 43.40 ± 5.46$^{ab}$ | 61.99 ± 3.32$^{ab}$ | 45.09 ± 5.83$^{ab}$ | 32.35 ± 1.77$^{ab}$ |
| SCGBT | 22.14 ± 5.46$^a$ | 41.76 ± 6.09$^a$ | 31.21 ± 1.60$^a$ | 25.37 ± 2.47$^a$ |
| AR | 25.10 ± 6.36$^a$ | 45.28 ± 8.58$^a$ | 32.42 ± 3.31$^a$ | 23.97 ± 2.46$^a$ |
| CCP | 40.66 ± 2.59$^{ab}$ | 56.79 ± 6.14$^{ab}$ | 40.44 ± 1.13$^{ab}$ | 28.44 ± 4.73$^a$ |
| AGR | 41.25 ± 6.00$^a$ | 61.28 ± 7.68$^{ab}$ | 44.34 ± 3.59$^{ab}$ | 31.17 ± 2.59$^{ab}$ |

Values are expressed mean ± S.D. of 5 mice 5.1. Changes in Numbers of CD34+ Cells in Blood and Bone Marrow The FACS results of CD34+ cells are shown in FIGS. 4 and 5. Based on the FACS results listed in Table 7, increases in the numbers of CD34+ cells in the blood and bone marrow were shown to be significant ($p<0.01$) in the hG-CSF control, compared to the normal medium control. In the groups to which the palmultang, *Capreolus capreolus ochracea* Thomas, and *Angelica gigas* extracts were administered, increases in the numbers of CD34+ cells in the blood and bone marrow were also shown to be significant ($p<0.01$), compared to the hG-CSF control. On the other hand, in the groups to which the SCGBT and *Astragalus membranaceus* Bunge var. *membranaceus* extracts were administered, changes in the numbers of CD34+ cells in the blood and bone marrow were not shown to be significant, compared to the hG-CSF control.

In the hG-CSF control, the number of CD34+ cells in the blood changed by 238.08%, compared to the normal medium control. In the groups to which the palmultang, SCGBT, *Astragalus membranaceus* Bunge var. *membranaceus*, *Capreolus capreolus ochracea* Thomas, and *Angelica gigas* extracts (200 mg/kg) were administered, the numbers of CD34+ cells in the blood changed by 61.89, −17.41, −6.39, 51.65, and 53.85%, respectively, compared to the hG-CSF control.

In the hG-CSF control, the number of CD34+ cells in the bone marrow changed by 83.14%, compared to the normal medium control. In the groups to which the palmultang, SCGBT, *Astragalus membranaceus* Bunge var. *membranaceus*, *Capreolus capreolus ochracea* Thomas, and *Angelica gigas* extracts (200 mg/kg) were administered, the numbers of CD34+ cells in the bone marrow changed by 48.29, 2.64, 6.62, 33.00, and 45.80%, respectively, compared to the hG-CSF control.

Based on the experimental results, it was revealed that the numbers of CD34+ cells in the blood and bone marrow significantly increased when the hG-CSF and palmultang extract were co-administered, compared to when the hG-CSF was administered alone.

5.2. Changes in Numbers of CD45+ Cells in Blood and Bone Marrow

The FACS results of CD45+ cells are shown in FIGS. 6 and 7. Based on the FACS results listed in Table 7, increases in the numbers of CD45+ cells in the blood and bone marrow were shown to be significant ($p<0.01$) in the hG-CSF control, compared to the normal medium control. In the groups to which the palmultang, *Capreolus capreolus ochracea* Thomas, and *Angelica gigas* extracts were administered, increases in the numbers of CD45+ cells in the blood and bone marrow were shown to be significant, compared to the hG-CSF control. On the other hand, in the groups to which the SCGBT and *Astragalus membranaceus* Bunge var. *membranaceus* extracts were administered, changes in the numbers of CD45+ cells in the blood and bone marrow were not shown to be significant, compared to the hG-CSF control.

In the hG-CSF control, the number of CD45+ cells in the blood changed by 312.39%, compared to the normal medium control. In the groups to which the palmnultang, SCGBT, *Astragalus membranaceus* Bunge var. *membranaceus*, *Capreolus capreolus ochracea* Thomas, and *Angelica gigas* extracts (200 mg/kg) were administered, the numbers of CD45+ cells in the blood changed by 44.38, −2.75, 5.45, 32.26, and 42.72%, respectively, compared to the hG-CSF control.

In the hG-CSF control, the number of CD45+ cells in the bone marrow changed by 87.18%, compared to the normal medium control. In the groups to which the palmultang, SCBBT, *Astragalus membranaceus* Bunge var. *membranaceus*, *Capreolus capreolus ochracea* Thomas, and *Angelica gigas* extracts (200 mg/kg) were administered, the number of CD45+ cells in the bone marrow changed by 31.35, 3.02, −2.68, 15.47, and 26.58%, respectively, compared to the hG-CSF control.

Based on the experimental results, it was revealed that the numbers of CD45+ cells in the blood and bone marrow significantly increased when the hG-CSF and palmultang extract were co-administered, compared to when the hG-CSF was administered alone.

Therefore, based on the results of Examples 5.1 and 5.2, it could be seen that the co-administration of the hG-CSF and palmultang extract caused a significant increase in proliferation of the bone-marrow-derived stem cells.

Example 6. Determination of Histopathologic Changes

Histopathologic changes of spleens and femoral bone marrow in eight groups were observed. The results are listed in the following Table 8.

TABLE 8

| Groups | Spleen | | | | Bone marrow Mean number of nuclear cells ($\times 10^2$ cells/mm$^2$) |
|---|---|---|---|---|---|
| | Total thickness (mm/central regions) | Number of white pulp (white pulp/mm$^2$) | Mean diameters of white pulp (μm/white pulp) | Mean number of red pulp nuclear cells ($\times 10^2$ cells/mm$^2$) | |
| Controls | | | | | |
| Intact vehicle | 1.58 ± 1.16 | 14.50 ± 2.37 | 459.22 ± 98.51 | 3.34 ± 0.80 | 16.30 ± 2.26 |
| hG-CSF | 1.86 ± 0.12a | 14.60 ± 1.84 | 478.38 ± 70.00 | 27.18 ± 5.19a | 74.51 ± 18.28a |
| Natural extract orally co-administered | | | | | |
| PMT | 1.63 ± 0.07b | 14.10 ± 2.33 | 493.19 ± 68.93 | 19.09 ± 2.44ab | 72.46 ± 11.54a |
| SCGBT | 2.06 ± 0.16ab | 14.00 ± 2.98 | 484.79 ± 84.57 | 28.92 ± 5.91a | 70.77 ± 11.22a |
| AR | 1.85 ± 0.18a | 14.80 ± 1.75 | 482.04 ± 116.86 | 30.65 ± 6.14a | 67.22 ± 10.57a |
| CCP | 2.00 ± 0.34a | 14.90 ± 2.60 | 487.78 ± 65.78 | 26.76 ± 3.43a | 80.03 ± 12.18a |
| AGR | 1.68 ± 0.14b | 14.60 ± 2.01 | 472.34 ± 65.60 | 17.61 ± 3.18ab | 67.30 ± 11.77a |

Values are expressed mean ± S.D. of 10 mice

6.1. Histopathologic Change of Spleen

As listed in Table 8, it was revealed that the splenomegaly findings caused by infiltration of nuclear cells in spleen red pulp were significant in the hG-CSF control. Also, it was revealed that increases in the total thickness of the spleens and the number of nuclear cells in the red pulp per unit area were significant (p<0.01), compared to the normal medium control, but the amount and diameters of the white pulp were observed to be similar to the normal medium control.

Figure 8:
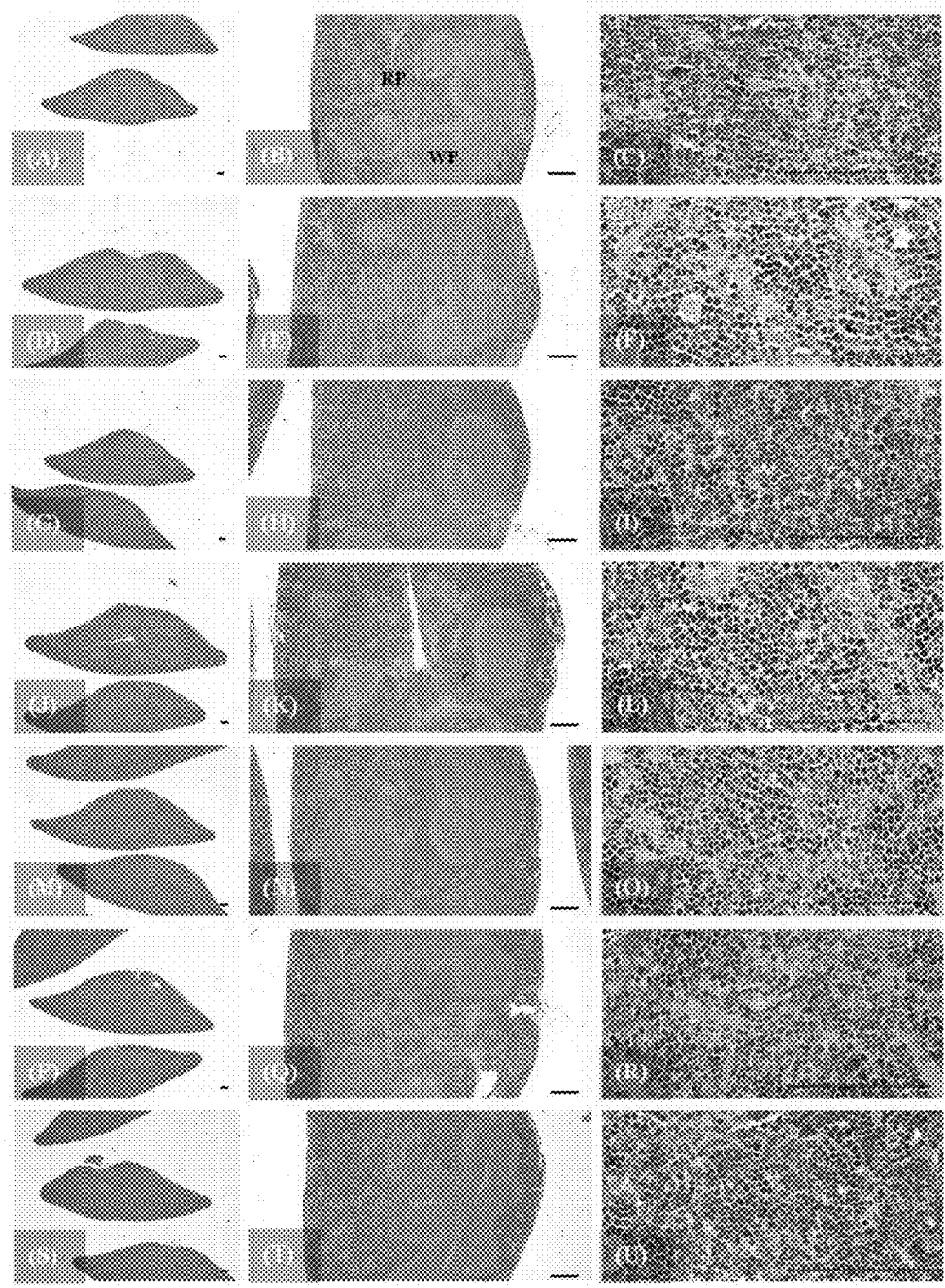
FIG. 8 is a diagram showing the results obtained by determining the total thicknesses of spleens of the mice into which the hG-CSF or the natural-substance-derived candidate compound is administered, and nuclear cells in red and white pulp of the mice per unit area (A to C: untreated, D to F: hG-CSF, G to I: palmultang+hG-CSF, J to L: SCGBT+hG-CSF, M to O: *Astragalus membranaceus* Bunge var. *membranaceus*+hG-CSF, P to R: *Capreolus capreolus ochracea* Thomas+hG-CSF, and S to U: *Angelica gigas*+hG-CSF).

FIG. 8 is an image showing the total thicknesses of the spleens and the number of nuclear cells in the red and white pulp per unit area. As shown in FIG. 8, it was revealed that decreases in in the total thickness of the spleens and the number of nuclear cells in the red pulp per unit area were significant (p<0.01) in the groups to which the palmultang and *Angelica gigas* extracts were administered, compared to the hG-CSF control, but an increase in the total thickness of the spleens was significant (p<0.01) in the SCGBT-administered group, compared to the hG-CSF control, and the histopathologic changes of the spleens were not significant in the groups to which the *Astragalus membranaceus* Bunge var. *membranaceus* and *Capreolus capreolus ochracea* Thomas extracts were administered, compared to the hG-CSF control.

In the hG-CSF control, the total thickness of the spleen changed by 17.47%, compared to the normal medium control. In the groups to which the palmultang, SCGBT, *Astragalus membranaceus* Bunge var. *membranaceus*, *Capreolus capreolus ochracea* Thomas, and *Angelica gigas* extracts (200 mg/kg) were administered, the total thicknesses of the spleens changed by −12.02, 10.72, −0.48, 7.81, and −9.75%, respectively, compared to the hG-CSF control.

In the hG-CSF control, the amount of spleen white pulp changed by 0.69%, compared to the normal medium control. In the groups to which the palmultang, SCGBT, *Astragalus membranaceus* Bunge var. *membranaceus*, *Capreolus capreolus ochracea* Thomas, and *Angelica gigas* extracts (200 mg/kg) were administered, the amounts of spleen white pulp changed by −3.42, −4.11, 1.37, 2.05, and 0.00%, respectively, compared to the hG-CSF control.

In the hG-CSF control, the mean diameter of the spleen white pulp changed by 4.17%, compared to the normal medium control. In the groups to which the palmultang, SCGBT, *Astragalus membranaceus* Bunge var. *membranaceus*, *Capreolus capreolus ochracea* Thomas, and *Angelica gigas* extracts (200 mg/kg) were administered, the mean diameters of the spleen white pulp changed by 3.09, 1.34, 0.77, 1.96, and −26%, respectively, compared to the hG-CSF control.

In the hG-CSF control, the amount of spleen red pulp per unit area changed by 714.75%, compared to the normal medium control. In the groups to which the palmultang, SCGBT, *Astragalus membranaceus* Bunge var. *membranaceus*, *Capreolus capreolus ochracea* Thomas, and *Angelica gigas* extracts (200 mg/kg) were administered, the amounts of spleen red pulp per unit area changed by −29.76, 6.39, 12.76, −1.55, and −35.21%, respectively, compared to the hG-CSF control.

6.2. Histopathologic Change of Femoral Bone Marrow

Figure 9:
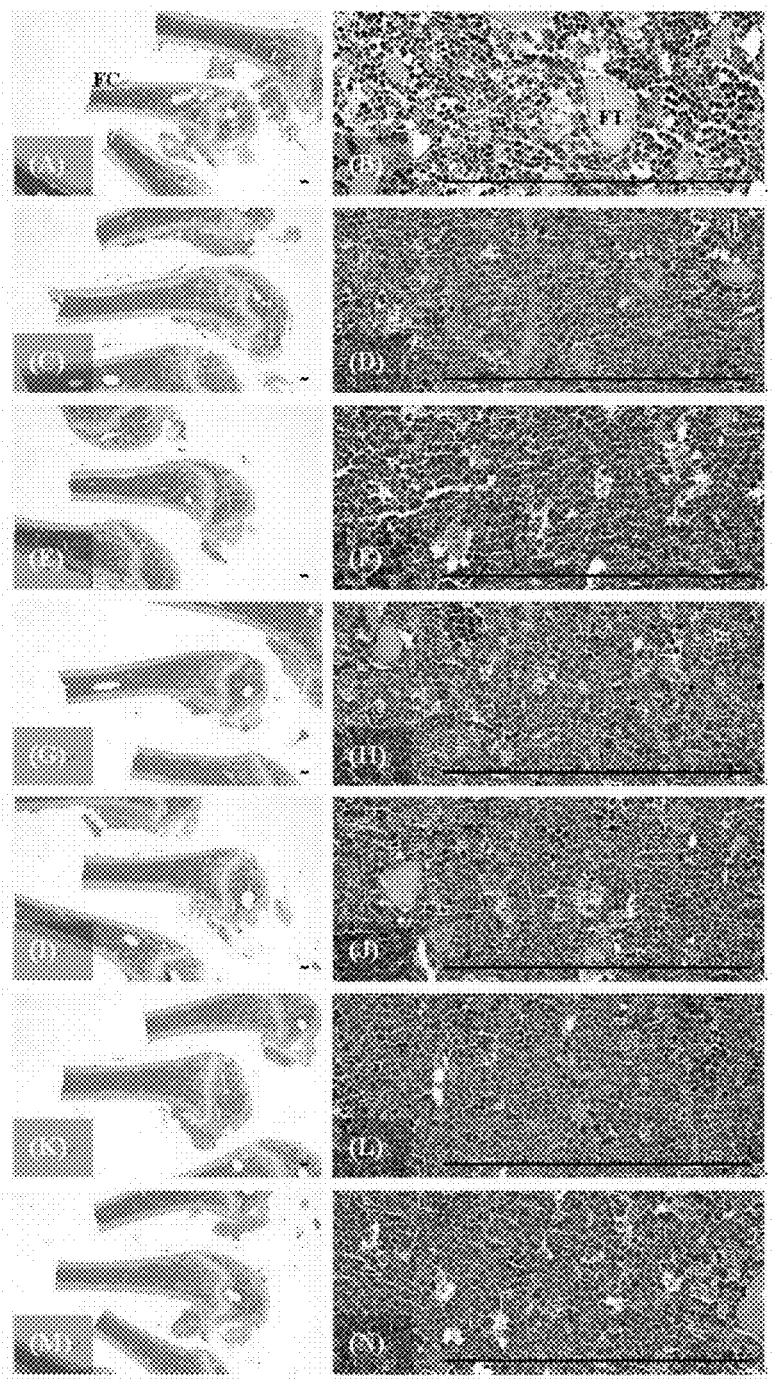
FIG. 9 is a diagram showing the results obtained by observing increases in the numbers of CD34 immunoreactive cells in the spleens and bone marrow of the mice into which the hG-CSF or the natural-substance-derived candidate compound is administered (A to B: untreated, C to D: hG-CSF, E to F: palmultang+hG-CSF, G to H: SCGBT+hG-CSF, I to J: *Astragalus membranaceus* Bunge var. *membranaceus*+hG-CSF, K to L: *Capreolus capreolus ochracea* Thomas+hG-CSF, and M to N: *Angelica gigas*+hG-CSF).

As listed in Table 8, it was revealed that the proliferation of the granulocytes was significant in the hG-CSF control. As shown in FIG. 9, it was revealed that an increase in the number of nuclear cells in the bone marrow per unit area was consequently significant (p<0.01), compared to the normal medium control, but the histopathologic changes of the femoral bone marrow were not significant in any of the groups to which the natural-substance-derived extracts were administered, compared to the hG-CSF control.

In the hG-CSF control, the number of nuclear cells in the femoral bone marrow per unit area changed by 357.02%, compared to the normal medium control. In the groups to which the palmultang, SCGBT. *Astragalus membranaceus* Bunge var. *membranaceus*, *Capreolus capreolus ochracea* Thomas, and *Angelica gigas* extracts (200 mg/kg) were administered, the numbers of nuclear cells in the femoral bone marrow per unit area changed by −2.75, −5.02, −9.79, 7.40, and −9.68%, respectively, compared to the hG-CSF control.

Based on the results of Examples 5.1 and 5.2, it could be seen that the side effects (e.g., splenomegaly) of hG-CSF were prevented and the number of leukocytes also increased when the hG-CSF and the palmultang extract were co-administered, compared to when the hG-CSF was administered alone.

Example 7. Determination of Immunohistochemical Changes

The numbers of CD34 and CD45 immunoreactive cells in the spleens and bone marrow in seven groups were observed. The results are listed in the following Table 9.

TABLE 9

| | Number of spleen immunoreactive cell (cells/mm$^2$) | | Number of bone marrow immunoreactive cell (cells/mm$^2$) | |
|---|---|---|---|---|
| Groups | CD34+ | CD45+ | CD34+ | CD45+ |
| Controls | | | | |
| Intact vehicle | 16.40 ± 2.72 | 44.90 ± 15.04 | 11.40 ± 3.92 | 35.80 ± 11.86 |
| hG-CSF | 133.40 ± 20.30$^c$ | 303.50 ± 79.69$^c$ | 46.20 ± 9.74$^c$ | 325.40 ± 98.79$^a$ |
| Natural extract orally co-administered | | | | |
| PMT | 174.60 ± 18.35$^{cd}$ | 405.21 ± 64.22$^{cd}$ | 74.20 ± 10.88$^{cd}$ | 490.10 ± 112.39$^{ab}$ |
| SCGBT | 137.70 ± 20.82$^c$ | 300.50 ± 70.36$^c$ | 41.30 ± 6.13$^c$ | 350.00 ± 70.41$^a$ |
| AR | 146.80 ± 14.77$^c$ | 327.50 ± 46.42$^c$ | 49.40 ± 8.83$^c$ | 364.90 ± 116.30$^a$ |
| CCP | 125.50 ± 13.74$^c$ | 478.80 ± 111.65$^{cd}$ | 42.20 ± 6.98$^c$ | 344.40 ± 102.18$^a$ |
| AGR | 160.60 ± 14.21$^{cd}$ | 462.40 ± 80.42$^{cd}$ | 81.00 ± 19.10$^{cd}$ | 536.70 ± 82.72$^{ab}$ |

Values are expressed mean ± S.D. of 10 mice

7.1. Changes in Numbers of CD34 Immunoreactive Cells in Spleen and Bone Marrow As listed in Table 9 and shown in FIG. 9, it was revealed that increases in the numbers of CD34 immunoreactive cells in the spleen and bone marrow were significant (p<0.01) in the hG-CSF control, compared to the normal medium control, and that increases in the numbers of CD34 immunoreactive cells in the spleens and bone marrow were significant (p<0.01) in the groups to which the palmultang and *Angelica gigas* extracts were administered, compared to the hG-CSF control. On the other hand, it was revealed that changes in the numbers of CD34 immunoreactive cells in the spleen and bone marrow per unit area were not significant in the groups to which the SCGBT, *Capreolus capreolus ochracea* Thomas, and *Astragalus membranaceus* Bunge var. *membranaceus* extracts were administered, compared to the hG-CSF control.

In the hG-CSF control, the number of CD34 immunoreactive cells in the spleen changed by 713.41%, compared to the normal medium control. In the groups to which the palmultang, SCGBT, *Astragalus membranaceus* Bunge var. *membranaceus, Capreolus capreolus ochracea* Thomas, and *Angelica gigas* extracts (200 mg/kg) were administered, the numbers of CD34 immunoreactive cells in the spleen changed by 30.88, 3.22, 10.04, −5.92, and 20.39%, respectively, compared to the hG-CSF control.

In the hG-CSF control, the number of CD34 immunoreactive cells in the bone marrow changed by 305.26%, compared to the normal medium control. In the groups to which the palmultang, SCGBT, *Astragalus membranaceus* Bunge var. *membranaceus, Capreolus capreolus ochracea* Thomas, and *Angelica gigas* extracts (200 mg/kg) were administered, the numbers of CD34 immunoreactive cells in the bone marrow changed by 60.61, −10.61, 6.93, −8.87, and 75.32%, respectively, compared to the hG-CSF control.

7.2. Changes in Numbers of CD45 Immunoreactive Cells in Spleen and Bone Marrow

Figure 10:
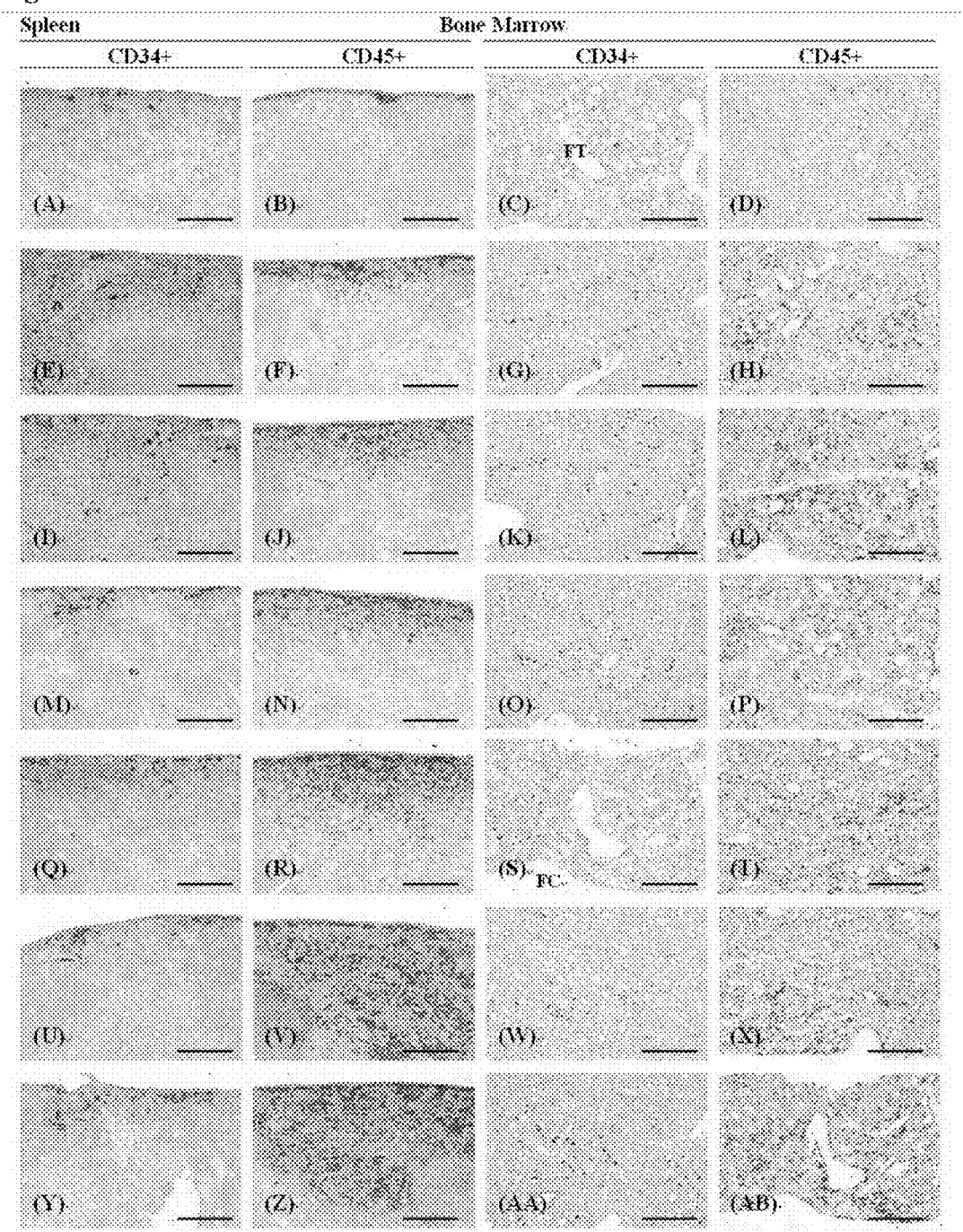
FIG. 10 is a diagram showing the results obtained by observing increases in the numbers of CD45 immunoreactive cells in the spleens and bone marrow of the mice into which the hG-CSF or the natural-substance-derived candidate compound is administered (A to D: untreated, E to H: hG-CSF, I to L: palmultang+hG-CSF, M to P: SCGBT+hG-CSF, Q to T: *Astragalus membranaceus* Bunge var. *membranaceus*+hG-CSF, U to X: *Capreolus capreolus ochracea* Thomas+hG-CSF, and Y to AB: *Angelica gigas*+hG-CSF).

As listed in Table 9 and shown in FIG. 10, it was revealed that increases in the numbers of CD45 immunoreactive cells in the spleen and bone marrow were significant (p<0.01) in the hG-CSF control, compared to the normal medium control, and that increases in the numbers of CD45 immunoreactive cells in the spleens and bone marrow were significant (p<0.01) in the groups to which the palmultang and *Angelica gigas* extracts were administered, compared to the hG-CSF control. On the other hand, it was revealed that an increase in the number of CD45 immunoreactive cells in the spleen was also significant (p<0.01) in the group to which the *Capreolus capreolus ochracea* Thomas extract was administered, compared to the hG-CSF control, but the number of CD45 immunoreactive cells in the bone marrow was observed to be similar to the hG-CSF control, and changes in the numbers of CD45+ cells in the blood and bone marrow were not significant in the groups to which the SCGBT and *Astragalus membranaceus* Bunge var. *membranaceus* extracts were administered, compared to the hG-CSF control.

In the hG-CSF control, the number of CD45 immunoreactive cells in the spleen changed by 575.95%, compared to the normal medium control. In the groups to which the palmultang, SCGBT, *Astragalus membranaceus* Bunge var. *membranaceus, Capreolus capreolus ochracea* Thomas, and *Angelica gigas* extracts (200 mg/kg) were administered, the numbers of CD45 immunoreactive cells in the spleens changed by 33.51, −0.99, 7.91, 57.76, and 52.36%, respectively, compared to the hG-CSF control.

In the hG-CSF control, the number of CD45 immunoreactive cells in the bone marrow changed by 808.94%, compared to the normal medium control. In the groups to which the palmultang, SCGBT, *Astragalus membranaceus* Bunge var. *membranaceus, Capreolus capreolus ochracea* Thomas, and *Angelica gigas* extracts (200 mg/kg) were administered, the numbers of CD45 immunoreactive cells in the spleens changed by 50.61, 7.56, 12.14, 5.84, and 64.94%, respectively, compared to the hG-CSF control.

Based on the experimental results, it was confirmed that the number of immunoreactive cells significantly increased when the hG-CSF and the palmultang extract were co-administered, compared to when the hG-CSF was administered alone.

In summary, the experimental results of Examples 2 to 7 showed that the increases in the weights of the spleens and the total numbers of nuclear cells in the blood and bone marrow by administration of the hG-CSF and the increases in the numbers of CD34+ and CD45+ cells in the blood and bone marrow were significant, and that the increases in the total thicknesses of the spleens and the numbers of nuclear cells in the red pulp and femoral bone marrow per unit area were significant in a histopathologic aspect, and the increases in the numbers of CD34 and CD45 immunoreactive cells in the spleens and hone marrow were significant in an immunohistochemical aspect.

Therefore, it was revealed that the proliferation and mobilization of the bone-marrow-derived stem cells by the hG-CSF significantly increased (p<0.01) when the palmultang extract was orally co-administered within 5 minutes, and the increases in the weight of the spleen and splenomegaly findings by proliferation of the nuclear cells in the red pulp were significantly inhibited (p<0.01), but the administration of the hG-CSF had no influence on the overall proliferation of the granulocytes.

Meanwhile, it was revealed that the proliferation and mobilization of the bone-marrow-derived stem cells were also significant in the group to which the *Capreolus capreolus ochracea* Thomas extract s administered, but the splenomegaly findings actually worsened, and that the co-administration of the SCGBT and *Astragalus membranaceus* Bunge var. *membranaceus* extracts had no influence on the effect of the hG-CSF on the proliferation and mobilization of the granulocytes and bone-marrow-derived stem cells, and had no influence on the side effects such as splenomegaly either.

Therefore, the palmultang extract is expected to provide a new combined medical system of Oriental and Western medicine which is very useful in improving an effect of the hG-CSF on mobilization of the bone-marrow-derived stem cells and reducing side effects such as splenomegaly.

The present invention has been described in detail. However, it should be understood that the detailed description and specific examples, while indicating preferred embodiments of the invention, are given by way of illustration only, and various changes and modifications within the spirit and scope of the invention will become apparent to those skilled in the art from this detailed description.

The invention claimed is:

1. A method for promoting proliferation of stem cells derived from bone marrow to treat a hematologic cancer, lymphoma, or bone marrow failure, comprising:
   administering a composition comprising a granulocyte colony-stimulating factor (GCSF) and a palmultang extract to a mammal in need thereof,
   wherein the GCSF is in an amount of between 0.001 and 300 mg/kg of body weight of the mammal,
   wherein the palmultang extract is in an amount of between 0.001 and 300 mg/kg of body weight of the mammal, and
   wherein said palmultang extract comprises
     15.5 wt % Angelicae Gigantis Radix
     15.5 wt % Atractylodis Rhizoma 14.3 wt % Cnidii Rhizoma
10.1 wt % *Ginseng* Radix Alba
11.4 wt % Glycyrrhizae Radix
0.8 wt % Hoelen
11.4 wt % Paeoniae Radix
21.0 wt % Rehmanniae Radix.

2. The method of claim 1, wherein the mammal has hematologic cancer, lymphoma or bone marrow failure.

3. The method of claim 1, wherein the stimulating factor and the palmultang extract are administered parenterally, orally, locoregionally, or percutaneously.

* * * * *